US009333178B2

(12) United States Patent
Duarte et al.

(10) Patent No.: US 9,333,178 B2
(45) Date of Patent: May 10, 2016

(54) ESSENTIAL OIL MICROPARTICLES AND USES THEREOF FOR PREVENTING ENTERIC DISEASES

(71) Applicants: Universidade Estadual de Campinas—UNICAMP, Campinas, São Paulo (BR); Ouro Fino Saúde Animal Ltda, São Paulo (BR)

(72) Inventors: Marta Cristina Teixeira Duarte, São Paulo (BR); Glyn Mara Figueira, São Paulo (BR); Mary Ann Foglio, São Paulo (BR); Rodney Alexandre Ferreira Rodrigues, São Paulo (BR); Dolivar Coraucci Neto, SãPaulo (BR); Ana Lúcia Tasca Goiz Ruiz, São Paulo (BR); João Ernesto de Carvalho, São Paulo (BR)

(73) Assignees: Universidade Estadual de Campinas—UNICAMP Brazilian State University, São Paulo (BR); Ouro Fino Saúde Animal LTDA., São Paulo (BR)

( * ) Notice: Subject to any disclaimer, the term of this patent is extended or adjusted under 35 U.S.C. 154(b) by 0 days.

(21) Appl. No.: 14/423,547

(22) PCT Filed: Aug. 26, 2013

(86) PCT No.: PCT/BR2013/000324
§ 371 (c)(1),
(2) Date: Feb. 24, 2015

(87) PCT Pub. No.: WO2014/028999
PCT Pub. Date: Feb. 27, 2014

(65) Prior Publication Data
US 2015/0209295 A1    Jul. 30, 2015

(30) Foreign Application Priority Data
Aug. 29, 2012 (BR) .......................... 1020120219751

(51) Int. Cl.
*A61K 9/50* (2006.01)
*A61K 36/899* (2006.01)

(52) U.S. Cl.
CPC .................. *A61K 9/50* (2013.01); *A61K 9/5036* (2013.01); *A61K 36/899* (2013.01)

(58) Field of Classification Search
None
See application file for complete search history.

(56) References Cited

U.S. PATENT DOCUMENTS

| 6,322,825 | B1 | 11/2001 | Ninkov |
| 2003/0157159 | A1 | 8/2003 | Franklin et al. |
| 2009/0186096 | A1* | 7/2009 | Kritzman et al. ............. 424/523 |
| 2010/0272818 | A1 | 10/2010 | Franklin et al. |

OTHER PUBLICATIONS http://kidshealth.org/PageManager.jsp?dn=KidsHealth&lic=1&ps=207&cat_id=20177&article_set=21964—accessed May 2015.*
Krishnan (Carbohydrate Polymers (2005), vol. 61, pp. 95-102).*
Prashar (Phytochemistry (2003), vol. 63, pp. 569-575).*
USDA website (http://plants.usda.gov/core/profile?symbol=CYCI)—accessed May 2015.*
Hur, J.; Lee, J.H. Comparative evaluation of a vaccine candidate expressing enterotoxigenico *Escherichia coli* (ETEC) adhesins for collibacilosis with a commercial vaccine using a pig model. *Vaccine*, v.30, p. 3829-3833, 2012.
Wu, S.; Zhang, F.; Huang, z.; Liu, H.; Xie, C.; Zhang, J.; Thacker, P.A.; Qiao, S. Effects of the antimicrobial peptide cecropin AD on performance and intestinal health in weaned piglets challenged with *Escherichia coli*. Peptides, v.35, p. 225-230, 2012.
Hayat, A.M.; Tribble, D.R.; Sanders, J.W.; Faix, D.J.; Shiau, D.; Armstrong, A.W.; Riddle, M.S. Knowledge, attitudes, and practice of travelers' diarrhea managemente among frontline providers. *Journal of Travel Medicine*, v. 18 (5), p. 310-317, 2011.
Licht, T.R.; Ebersbach, T, Frokiaer, H. Prebiotics for prevention of gut infection. *Trends in Food Science & Technology*, v.23, p. 70-82, 2012.
Li, S.Y.; Ru, Y, J.; Liu, M.; Xu, B.; Péron, A.; Shi, X.G, The effect of essential oils on performance, immunity and gut microbial population in weaner pigs, Livestock Science, v. 145, p. 119-123, 2012.
Junior, V.F.V.; Pinto, A.C.; Maciel, M.A.M. Plantas medicinas, cura segura? Quimica Nova, v. 28 (3), 519-528, 2005.
Skehan P., Storeng R., Scudiero D., Monks A., McMahon J., Vistica D., Warren J.T., Bokesch H., Kenney S., Boyd M.R. New colorimetric citotoxicity assay for anticancer-drug screening. Journal of the National Cancer Institute, v. 82 (13), p. 1107-1118, 1990.
Fouche, G.; Cragg, G.M.; Pillay, P.; Kolesnikova, N.; Maharaj, V.J.; Senabe, J. In vitro anticancer screening of South African plants. Journal of Ethnopharmacology, v. 119, p. 455-461, 2008.
Shoemaker, R.H. The NCI60 human tumour cell line anticancer drug screen. Nat Ver Cancer, v. 6, p. 813-823, 2006.
OECD Guideline for Testing of Chemicals—Acute Oral Toxicity: 420—adopted Dec. 17, 2001. "Sistema Globalmente Harmonizado de Classificação e Rotulagem de Substâncias Quimicas" (Globally Harmonized System of Classification and Labelling of Chemicals—GHS) http://www.unece.org/trans/danger/publi/ghs/officialtext.html.

(Continued)

*Primary Examiner* — Susan Hoffman
(74) *Attorney, Agent, or Firm* — Brinks Gilson & Lione (57) ABSTRACT

The present invention relates to a microparticle containing essential palmarosa and lemongrass oils for controlling enteric diseased caused by microorganisms. More specifically, the microparticle according to the present invention can be used for controlling enteric infections caused by pathogenic bacteria in humans and animals, and can be used as an alternative to the administration of antibiotics for that purpose. The microparticle can be used in the veterinary and pharmaceutical fields and can be administered orally.

11 Claims, 3 Drawing Sheets

(56) References Cited

OTHER PUBLICATIONS

Rodrigues, RAF Preparo, caracterização e avaliação funcional de rnicrocápsulas obtidas por spray drying, contendo extrato de café crioconcentrado. Fac Eng Alimentos UNICAMP, 2004.
United Nations, New York and Geneva, 2011, "Globally Harmonized System of Classification and Labelling of Chemicals (GHS)" Fourth Revised Edition, pp. 1-568.
Ahmad, Mehraj et al., "Physico-mechanical and antimicrobial properties of gelatin film from the skin of unicorn leatherjacket incorporated with essential oils", *Food Hydrocolloids* 28 (2012), pp. 189-199.
Ahmad, Mehraj et al., "Quality changes of sea bass slices wrapped with gelatin film incorporated with lemongrass essential oil", *International Journal of Food Microbiology* 155, (2012), pp. 171-178.
Chagas, Ana Carolina S. et al., "II Simpósio sobre Inovação e Criatividade Cientifica na Embrapa", *Embrapa* (Apr. 28-30, 2010).
Donsi, Francesco et al., "Nanoencapsulation of essential oils to enhance their antimicrobial activity in foods", *LWT—Food Science and Technology*, 44, (2011), pp. 1908-1914.
Durarte, Marta Cristina Teixeira et al., "Activity of essential oils from Brazilian medicinal plants on *Escherichia coli*", *Journal of Ethnopharmacology*, 111 (2007), pp. 197-201.
Gutierrez, J., Barry-Ryan, C., Bourke, P., "The anti-microbial efficacy of plant essential oil combinations and interactions with food ingredients", *International Journal of Food Microbiology*, vol. 124, Issue 1, (May 10, 2008), pp. 91-97.
Krishnan, Savitha; Bhosale, Rajesh; Singhal, Rekha S., "Microencapsulation of cardamom oleoresin: Evaluation of blends of gum Arabic, maltodextrin and a modified starch as wall materials", *Carbohydrate Polymers*, vol. 61, Issue 1, (Jul. 2005), Abstract.

\* cited by examiner

ESSENTIAL OIL MICROPARTICLES AND USES THEREOF FOR PREVENTING ENTERIC DISEASES

CROSS-REFERENCE TO RELATED APPLICATIONS

This application claims the benefit of priority to PCT/BR2013/000324, filed Aug. 26, 2013, which claims priority to Brazilian Patent No. BR 10 2012 021975 1, filed Aug. 29, 2012, the entire contents of which is incorporated herein by reference.

FIELD OF THE INVENTION

The present invention is a microparticle containing *Cybopogon citratus* and *Cymbopogon martinii* essential oils for the control of enteric diseases caused by microorganisms. More specifically, the microparticle of the present invention can be used in the control of enteric infections caused by pathogenic bacteria in humans and animals, being able to be used as an alternative to antibiotics for this purpose. The microparticle can be employed in veterinary and pharmaceutical industry and can be administered orally.

BACKGROUND OF THE INVENTION

Currently, the digestive tract infections are caused by pathogenic and opportunistic microorganisms. As an example, we mention the toxigenic strains of *Escherichia coli* (ETEC) which produce enterotoxins that cause diarrhea and dehydration both in humans, known as traveler's diarrhea, and in animals, called colibacillosis.

In humans, ETEC is the most common cause of traveler's diarrhea, which affects millions of visitors in tropical and subtropical risk areas every year. These pathogens can be acquired by ingesting contaminated food and water. In the veterinary sector, the production of pork is successful chain in Brazilian agribusiness. The enteric colibacillosis is the disease with the highest Impact on the pig farming industry, not limited to it. Therefore, it is still common to use chemical additives in feed as growth promoters. However, therapeutic and prophylactic products may leave residues in edible products, contaminate the ecosystem and develop resistant microbial strains.

Given these problems, some government agencies in several countries have been limiting the use of antimicrobials, in addition to banning them as animal growth promoters, which are demanding the search for alternatives to the use of these substances.

Among the viable alternatives for the replacement of antimicrobials as growth promoters are the development and application of vaccines, control of environmental conditions for the creation, and use of feed (diet) with the appropriate use of prebiotics, probiotics, synbiotics, enzymes and compounds of vegetables.

The work of Hur and Lee (2012) compares the effects of a vaccine candidate against ETEC to the obtained by a commercial vaccine, revealing that the candidate developed by the research group is promising in fighting the *coli* bacillosis. However, the preparation of the vaccine involves the study of genes that cause ETEC virulence, the insertion of these genes into a plasmid and the transfection of plasmids into an attenuated microorganism and then for the animals immunization. The microparticle proposed in the present invention dispenses the use of genetic engineering techniques that, in addition to make the product more expensive, also presents efficacy, safety and ethical and social aspects as barriers to marketing.

Additives to food to replace antibiotic has been proposed and shown to be effective in combating ETEC. The work of Wu at al. (2012) shows that the peptide cecropin AD added to the basal diet in a proportion of 400 mg/kg have efficacy in increasing immunity and retention of nitrogen and energy, as well as the reduction of intestinal pathogens in weaned piglets. However, cecropin AD used in this work was obtained by isolation of *Hyalophora cecropia* and its expression in genetically modified microorganism *Bacillus subtilis*, a process that requires the purification of the used substance and whose practical results of applying the diarrhea control in porcines was found to be intermediate to the control group and the group treated with antimicrobials (kitasamycin 100 mg/kg and colistin sulfate 800 mg/kg). The microparticle proposed in the present invention showed to have similar activity to antibiotics and to be superior to the used control.

The document CN102178115 dated May 13, 2011, relates to a composition comprising different corn-, soybean-, calcium- and fish-derived products for addition to food (premix) of weaned piglets. The alleged advantage for the final composition (premix reinforced with corn-, soy-, calcium- and fish-derived products) is to solve problems of immune failure, secretion of digestive enzymes, low development of the digestive tract and frequent diarrhea in these animals. However, there is no part of the composition containing vitamins, minerals and enzymes that acts directly on ETEC or other pathogenic microorganisms.

In humans, the work of Hayat et al. (2011) shows that the current practice in the travelers diarrhea control is present in education, aggressive fluid replacement, antidiarrheal therapy, and the use of antimicrobials. However, there is concern about the irrational use of antimicrobials due to induction of bacterial resistance. Alternatively, there is evidence that a form of control of infections of the digestive tract, according to Licht et al. (2012), is the use of probiotics capable of selectively stimulate the growth of intestinal beneficial bacteria in the colon. However, the absence of publications with negative results may represent a bias in confirming the use of prebiotics as a method of controlling or preventing these infections.

Patent US20030157159, dated Aug. 21, 2003, describes a composition containing terpenes and a surfactant in the ratio of 1 to 99%, which are useful for the prevention or treatment of infections of the digestive tract in animals and humans. It also proposes the inclusion of the referred terpenes in liposomes. However, the in vitro antimicrobial activity to various pathogens reported in this document is demonstrated by the mixture of terpenes not included in liposomes, which serve to stabilize the mixture to actual use. The microparticles of the present invention are obtained by microencapsulation of *Cymbopogon citratus* and *Cymbopogon martinii* oils with soluble walls, which gives better product solubility in water due to the fact that rely on a process to obtain an emulsion and contain a surfactant as an auxiliary. As it is originally an oil, this is an advantage in terms of absorption in the animal, since the use is oral.

The work of Li et al. (2012), as well as the document WO2008/155536, dated Jun. 18, 2007, relates to a supplement for feeding piglets with the present invention microencapsulated essential oils, mainly containing cinnamaldehyde, which is able to increase food intake, rate growth and diarrhea incidence in animals, but it is a compound relatively toxic and allergenic (Junior et al., 2005). The present invention, however, proposes a microparticle containing micro encapsulated *Cymbopogon citratus* and *Cymbopogon martinii* essential oils, whose antimicrobial activity, when in combination, is greater than the activity of the two oils isolated. Such microparticle presents safe use and demonstrates in vitro antimicrobial effect and satisfactory performance when used in the feed of porcines in the nursery phase, with potential use in replacement to antibiotics used as growth promoters in animals and as a gastrointestinal infections prophylactic microparticle in humans.

In view of the prior art, the present invention has advantages in several aspects. First, the technique of microencapsulation by spray-dryer is a well-established industrial technique easily implemented from laboratory scale to the industrial scale. Microencapsulation provides a product stable to external agents such as oxygen and light, especially during the product storage.

The present invention is applicable in the pharmaceutical and veterinary fields for the prevention of gastrointestinal infections caused by enterobacteria such as *Escherichia coli* ETEC, especially as a growth promoter in the feed of porcines.

BRIEF DESCRIPTION OF THE INVENTION

The present invention relates to a microparticle comprising of *Cymbopogon citratus* and *Cymbopogon martinii* essential oils, a wall material for the formation of microparticles, an emulsifying agent and the inclusion or not of the microparticles in pharmaceutical and/or veterinary acceptable vehicles, in food, water or any others that are orally administered.

The microparticle of the invention can be applied in prevention of gastrointestinal infections caused by pathogenic bacteria in humans and animals. Currently, it is still common to use chemical additives in the feed and the use of antimicrobials, which has been forbidden by some government agencies for leaving residues in edible products, contaminating the ecosystem and developing resistant microbial strains. The present invention can be used as an alternative to this issue.

DETAILED DESCRIPTION OF THE INVENTION

The present invention relates to a microparticle comprising the following components:
*Cymbopogon citratus* essential oil;
*Cymbopogon martini* essential oil;
microparticles wall material, and
emulsifying agent.

The microparticle may contain the ratios of 1:3, 1:1 or 3:1 of essential oils of *Cymbopogon citratus* and *Cymbopogon martinii*, preferably 3:1.

The essential oils of *Cymbopogon citratus* and *Cymbopogon martinii* can be obtained by hydrodistillation, by steam distillation or other processes that allow obtaining it.

The wall material can be selected from the group of Arabic gum, maltodextrin, chitosan, cashew tree gum, among others or a mixture thereof, preferably maltodextrin.

The microparticle coating can be obtained by any method known in the art, which allows oils micro-encapsulation, for example, by Rodrigues (2004).

The emulsifier may be selected from the group of Tween 80, 60, or 20, soy lecithin, among others, which is preferably Tween 80.

The microparticle has variable size between 100 and 1000 µm and spherical shape.

The objective of its application is to prevent infections of the gastrointestinal tract caused by pathogenic bacteria in humans and animals.

The microparticles may be administered in its original form or in vehicles pharmaceutically and/or veterinary acceptable in the form of tablets, emulsion, suspension, gel capsule, among others.

Additionally, the microparticles of the present invention can be mixed with water, food, animal feed or any other for oral administration.

Preparation of *Cymbopogon citratus* and *Cymbopogon martinii* Essential Oils Microparticles.

For the preparation of microparticles was performed a process known in the art. The wall material was dissolved in distilled water with a stir plate. The oils and a emulsifier agent were added to the preparation and homogenized. After homogenization, the formulation was passed through the mini spray dryer. The operating conditions for microencapsulation were optimized by varying the inlet temperature of 180° C.±5° C., the ratio of oil (20% compared to maltodextrin) and a total of solids of 30%. The carrier gas used was $N_2$.

EXAMPLES

Example 1

Antimicrobial Activity of *Cymbopogon* Spp Essential Oil for *E. Coli* in Different Seasons The antimicrobial activity of *Cymbopogon citratus* and *Cymbopogon martinii* oils for different *E. coli* isolates as well as for the standard strain was evaluated by broth microdilution assay, in accordance with the M7-A6 standard (CLSI, 2003). In a sterile 96-well microplate were deposited 100 µL of Luria broth (*E. coli*), whereas the column 12 was used for the control of microorganism and culture medium sterility. To the Lane 1—line A were added 50 µL of essential oil solution of known concentration, and further were added 50 µL of medium, these ones related to the control of the samples sterility.

Then, 100 µL of the same materials were added in line B, the content of the homogenized wells with medium and transferred to the wells of the next line (C), repeating this procedure until the line H, so as to obtain a concentration decreasing of the material. 100 mL of residue were discarded. Then, 100 µL of microorganism inoculum, which turbidity was compared to the 0.5 McFarland scale and diluted to a final concentration of $10^4$ cells/ml, were added. The plates were sealed with Parafilm® and incubated for 24 hours at 36° C. Alter the incubation period, 50 µL of a solution of triphenyl tetrazolium chloride—TTC (0.5%) were added and the plates were reincubated for 3 h. The MIC was defined as the lowest sample concentration, capable of preventing the appearance of the red color, given to the medium when the cells have respiratory activity, that is, when there was growth of the microorganism.

It was also included in the assay the gentamicin sulfate antibiotic control, as well as a control to confirm the sterility of the culture medium and the microorganism growth.

The activity of C. citratus and C. martinii oils was also evaluated from the mixture thereof (the present invention) in different ratios, i.e., 75:25, 25:75 and 50:50 (w/w). The MIC results (Minimum Inhibitory Concentration—mg/ml) are shown in Table 1.

TABLE 1

Antimicrobial activity (MIC - mg/ml) of the essential oil of aromatic species for E. coli, depending on the season. The oils were tested individually and in different proportions.

| Season (2009) | E. coli strain | Cc | Cm | Cc + Cm (75:25) | Cc + Cm (25:75) | Cc + Cm (50:50) |
|---|---|---|---|---|---|---|
| Summer | ATCC11775 | 0.8 | 1.0 | 0.5 | 0.5 | 0.7 |
| | MB 0016 | 1.4 | 1.6 | 0.9 | 0.9 | 1.0 |
| | MB 0020 | 1.0 | 1.0 | 0.6 | 0.8 | 0.8 |
| | MB 0021 | 1.8 | 1.0 | 1.0 | 1.0 | 1.0 |
| | MB 0022 | 1.5 | 1.7 | 1.0 | 1.0 | 1.0 |
| | MB 0024 | 1.2 | 1.5 | 1.0 | 1.0 | 1.0 |
| | MB 0025 | 1.1 | 1.0 | 0.8 | 1.0 | 0.9 |
| Autumn | ATCC11775 | 0.5 | 0.5 | 0.5 | 0.4 | 0.5 |
| | MB 0016 | 0.4 | 0.46 | 0.25 | 0.1 | 0.4 |
| | MB 0020 | 0.8 | 0.93 | 0.8 | 0.9 | 1.46 |
| | MB 0021 | 1.1 | 1.2 | 1.0 | 0.9 | 1.46 |
| | MB 0022 | 1.1 | 0.9 | 1.0 | 1.0 | 1.0 |
| | MB 0024 | 1.0 | 1.0 | 1.0 | 1.0 | 1.0 |
| | MB 0025 | 1.0 | 0.9 | 0.7 | 0.7 | 0.8 |
| Winter | ATCC11775 | 0.5 | 0.5 | 0.5 | 0.5 | 0.5 |
| | MB 0016 | 1.0 | 0.5 | 1.0 | 0.5 | 1.0 |
| | MB 0020 | 0.5 | 0.5 | 0.5 | 0.5 | 0.5 |
| | MB 0021 | * | 1.0 | * | 1.0 | 1.0 |
| | MB 0022 | 1.6 | 1.0 | 1.0 | 1.0 | 1.0 |
| | MB 0024 | * | 0.9 | 1.6 | 0.9 | 1.0 |
| | MB 0025 | * | * | 1.7 | 1.0 | 1.2 |
| Spring | ATCC11775 | 1.0 | 0.25 | 0.35 | 0.5 | 0.5 |
| | MB 0016 | 0.12 | 0.5 | 0.5 | 0.5 | 0.25 |
| | MB 0020 | 1.1 | 0.6 | 0.9 | 0.8 | 1.0 |
| | MB 0021 | * | 1.0 | 1.0 | 1.0 | 1.0 |
| | MB 0022 | * | 1.1 | 1.3 | 1.0 | 1.0 |
| | MB 0024 | 1.4 | 1.0 | 1.2 | 1.0 | 1.0 |
| | MB 0025 | 1.3 | 1.0 | 1.1 | 1.0 | 1.0 |

*MIC > 2.0 mg/mL;
Cc = Cymbopogon citratus,
Cm = C. martinii

The results in Table 1 show that, in general, all oil combinations yielded better activities than when they were tested separately.

According to the results we can state that the species C. martinii (palmarosa) proved to be the most active against different strains of E. coli isolated from porcines with diarrhea, with wide spectrum of action, with best activities between autumn and winter. However, the mixture of the C. citratus and C. martinii oils in the ratio 25:75 (1:3) or 75:25 (3:1) incurred even better activities.

Example 2

In Vitro Cytotoxicity of the Cymbopogon Citratus and Cymbopogon Martinii Essential Oils of the Present Invention The in vitro cytotoxicity of essential oils (present invention) were evaluated against two normal cell lines (VERO—African green monkey kidney epithelial cells and HaCat—immortal human keratinocytes) and against a panel of human tumor cells.

Based on the results, growth rate graphics from the sample concentration for each of the tested strain were generated. Three effective concentrations called $GI_{50}$ (growth inhibition, the concentration required to disrupt 50% cell growth), TGI (total growth inhibition, the concentration required for 0% of cell growth) and $LC_{50}$ (lethal concentration, concentration required for 50% cell death) could be calculated by nonlinear regression, sigmoidal, using 8.0 Origin software.

Figure 1:
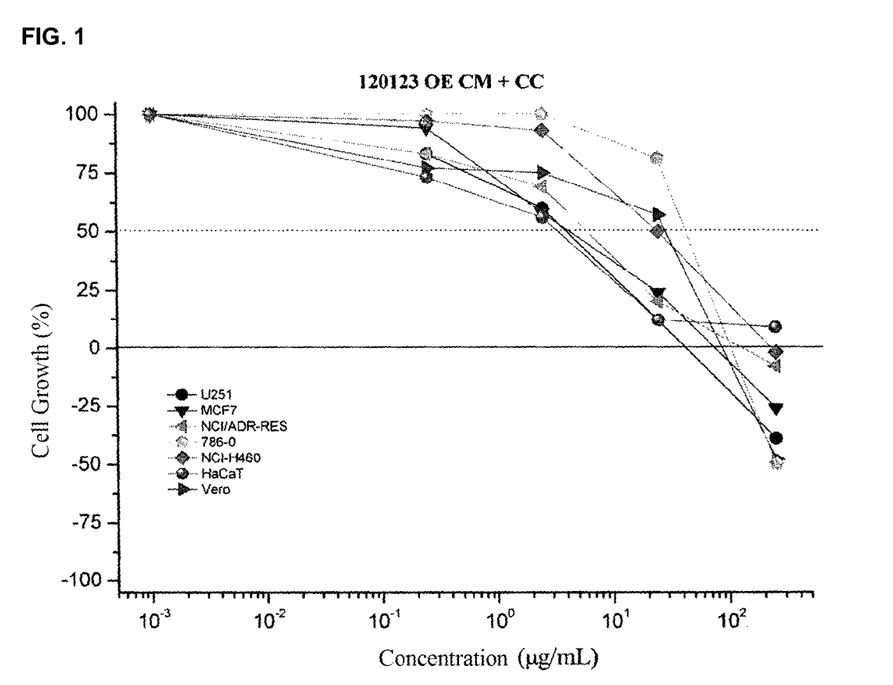
FIG. 1 shows the cell growth (%) of human tumor cells in the presence of the present invention in a toxicity assay in vitro.

The test results obtained are shown in FIG. 1 (present invention) and table 2. In this model, one way to infer the growth rate is by spectrophotometric reading of the absorbance of cellular proteins stained with sulforhodamine B (SRB), an anionic dye staining bright pink. This dye can bind to protein terminations of basic amino acids in living cells fixed with Trichloroacetic acid (TCA), thus being an independent assay of cell metabolism and allowing a sensitive measurement of protein linearly with the number of cells in culture. The SRB assay is considerably fast, simple and shows sensitivity comparable to those fluorescent assays and upper to the assays that use visible dyes, even at low cell concentrations (1000 to 2500 cells per chamber) (Skehan et al, 1990).

TABLE 2

Values of TGI effective concentration (μg/ml, Total Growth Inhibition - concentration needed for cell growth does not occur) of present invention and of doxorubicin.

| | 2 | m | a | 7 | 4 | TGI Average* | V | q |
|---|---|---|---|---|---|---|---|---|
| Doxorubicin | 1.24 | >25 | >25 | >25 | >25 | >25 | NT | >25 |
| C. martini/and C. citratus microparticles | 43.1 | 72.9 | 127.3 | 127.3 | 217.9 | 117.7 | 84.2 | >250 |

Human Cell Lines: 2 = U251 (glioma, CNS); m = MCF-7 (breast); a = NCI-ADR/RES (ovary, with multidrug resistant phenotype); 7 = 786-0 (kidney); 4 = NCI-H460 (lung, non-small cells), V = VERO (African green monkey kidney epithelial cells); q = HaCat (keratinocyte, immortalized normal cell).
NT = Not tested.
TGI: Total Growth Inhibition, concentration required for occuring total inhibition of the cell growth; *Mean TGI: arithmetic mean of the values for TGI tumor lines.
Parameters for evaluation of activity on tumor cell lines: inactive (mean TGI > 50 μg/ml), weak activity (15 μg/ml < mean TGI < 50 μg/ml), moderate activity (6.25 μg/ml < mean TGI < 15 μg/ml) and potent activity (mean TGI < 6.25 μg/ml) (Fouche et al. 2008)

This test allows us to evaluate the antitumor activity through exposure of human tumor cells in exponential growth phase at different concentrations of the sample and whether that exposure led to an interruption in the growth rate without cell death (cytotoxic activity) or caused the death cell (cytocidal activity). To measure the activity, an effective concentration called TGI (total growth inhibition, concentration required for 0% cell growth occurs) (Shoemaker, 2006) was calculated.

Chemotherapy doxorubicin was used as positive control. In addition to a standard of comparison, the main purpose of using this control was to verify that all employed cell lines kept the profile of response to chemotherapy. This is because with successive passages necessary for the maintenance of cell culture, there is the possibility of changing the lineage in culture, and this mutation could be detected by the change in response against doxorubicin. Furthermore, in order to minimize the occurrence of mutations, the cell lines are perpetuated only by up to 20 passages, after which they are replaced by new cells of the same strain that were maintained frozen.

With respect to the normal strains, the present invention exhibited antiproliferative activity of weak to moderate on the VERO line (TGI 84.2 µg/mL) for *C. martinii* and *C. citratus* (Table 2), suggesting a small cytotoxic action on kidney cells. However, the analysis of the in vivo tests showed that the in vitro effect did not translate into toxicity in animals evaluated. Otherwise, the present invention did not interfere with the human keratinocytes cell line growth (HaCaT), with TGI values >250 µg/ml at the maximum tested concentration (Table 2).

As the action on human tumor cell lines, the present invention was tested inactive, since the TGI was above the limit set for activity (50 µg/ml).

Example 3

Test of Acute Toxicity in Rodents (OECD, 2001)

The object of the present invention, the microparticle of 3:1 *Cymbopogon citratus* and *Cymbopogon martinii* essential oils was administered in a single dose of 5000 mg/kg to five animals, namely: pet 2.1 (preliminary test) and animals 2.2 to 2.5 (main test). Five additional animals (identified as 3.1 to 3.5) did not received any oral treatment, being considered as a second control group ("satellite") of the experiment.

Figure 3:
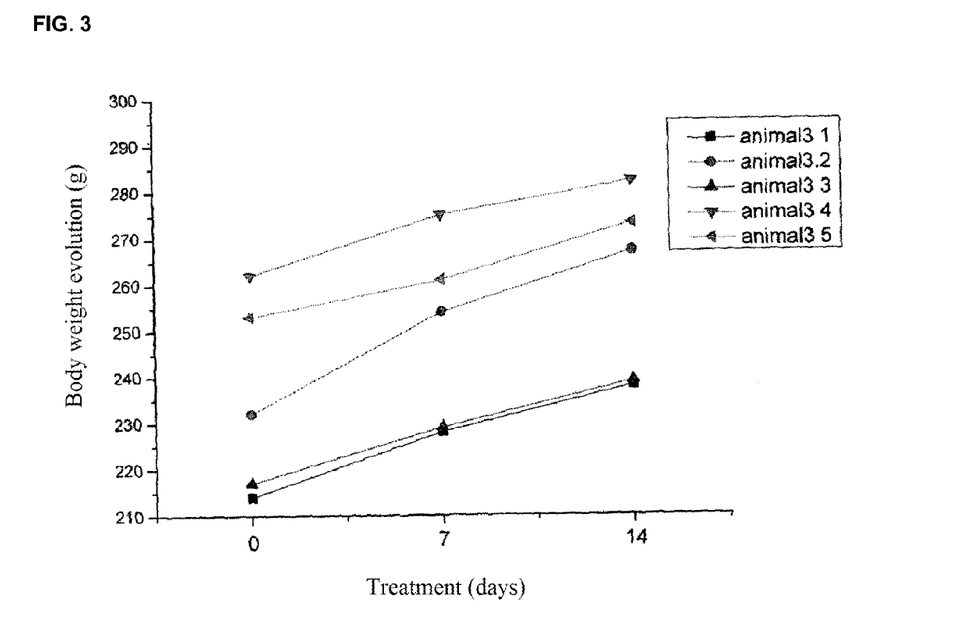
FIG. 3 shows the evolution of animal body weight in Wistar/Uni mice without treatment (group "satellite") during the period of 14 days. This result is part of an in vivo toxicity assay.

Twenty-four hours after administration of the present invention oral dose of 5000 mg/kg, piloerection was observed in all experimental animals, the appearance being normalized by 48 hours after start of the test. In the subsequent days, the individual clinical assessment of experimental animals, including appearance (general condition of the animal, and skin and fur changes), body weight evolution, clinical signs (heart and respiratory rate), spontaneous behavior (hyperactivity/lethargy) and response to stimuli (changing reflections) showed no changes in behavior and mood, motor activity, muscle tone, reflexes, central and autonomic nervous system activity. Throughout the trial period, it was possible to smell the characteristic odor of the essential oils exhaled by animals. At the end of the trial, at the time of euthanasia, all the animals were healthy. Table 3 shows the corresponding values of the body weight evolution per animal during the experimental period of the animals treated with the present invention and the animals receiving no treatment ("Satellite").

same feed ("satellite" group—FIG. 3), the experimental animals showed weight gain compatible with normality. The statistical analysis (Duncan test) in weight gain between the group treated with the present invention and the "satellite" control revealed no significant difference, suggesting the non-toxicity of the present invention. At the end of the experimental period (14 days), necropsy of all the animals and histopathological analysis was performed and revealed no evidence suggestive of toxicity. Using the GHS chemicals classification system, the microparticles of the present invention were classified as nontoxic after a single dose ($LD_{50}$ greater than 5000 mg/kg).

According to the results of the acute oral toxicity test in rodents, the present invention showed no systemic toxic effects that could be shown in adult Wistar/Uni rats after single oral administration at a dose of 5000 mg/kg. Following the GHS ("Globally Harmonized System of Classification and Labelling of Chemicals") classification for acute toxicity tests, the microparticles of the present invention were classified as nontoxic after a single dose ($LD_{50}$ greater than 5000 mg/kg). Experimental animals treated with the present invention with a single dose of 5000 mg/kg showed no systemic toxic effects that could be shown, with a body weight gain consistent with the same age ("Satellite" group). The uniformity in weight gain between the experimental groups was statistically analyzed by Duncan's test ($p>0.05$), corroborates this assertion. After euthanasia, no macroscopic changes suggestive of toxicity in vital organs were detected.

Example 4

Performance Evaluation and Score of Diarrhea in Nursery Phase in Piglets Fed with the Present Invention in the Preferred Embodiment The present invention (ratio 3:1) was evaluated on performance and score of diarrhea in piglets in the nursery phase (treatment CB006-S). For this evaluation, 72 piglets of both sexes with starting age of 28 days and terminal of 63 days. 4 piglets were housed in each pen (two males and two females)

TABLE 3

Effect of acute oral administration in Wistar/Uni rat on the evolution of body weight during the 14 days after a single administration of the microparticles of the present invention as well as the animals in the control group ("Satellite") (ANOVA: F (2, 12) = 0.17 Duncan Test p > 0.05).

| Group | Animal | Initial Weight (g) | Adm. Vol. (ml) | Weight in 7 days (g) | Final Weight (g) | Total Weight Gain (g) | Deaths |
|---|---|---|---|---|---|---|---|
| present | 2.1 | 310 | 3.1 | 333 | 346 | 36 | 0 |
| invention | 2.2 | 285 | 2.85 | 310 | 316 | 31 | 0 |
| | 2.3 | 305 | 3.05 | 327 | 321 | 16 | 0 |
| | 2.4 | 332 | 3.32 | 356 | 366 | 34 | 0 |
| | 2.5 | 306 | 3.06 | 306 | 314 | 12 | 0 |
| mean ± dpm | | 306.8 ± 16.9 | | 326.4 ± 20.0 | 332.6 ± 22.6 | 25.8 ± 11.0 | |
| Satellite | 3.1 | 214 | — | 228 | 238 | 24 | 0 |
| | 3.2 | 232 | — | 254 | 267 | 35 | 0 |
| | 3.3 | 217 | — | 229 | 239 | 22 | 0 |
| | 3.4 | 262 | — | 275 | 232 | 20 | 0 |
| | 3.5 | 253 | — | 261 | 273 | 20 | 0 |
| mean ± dpm | | 235.6 ± 214 | | 249.4 ± 20.5 | 259.8 ± 20.2 | 24.2 ± 6.3 | |

Figure 2:
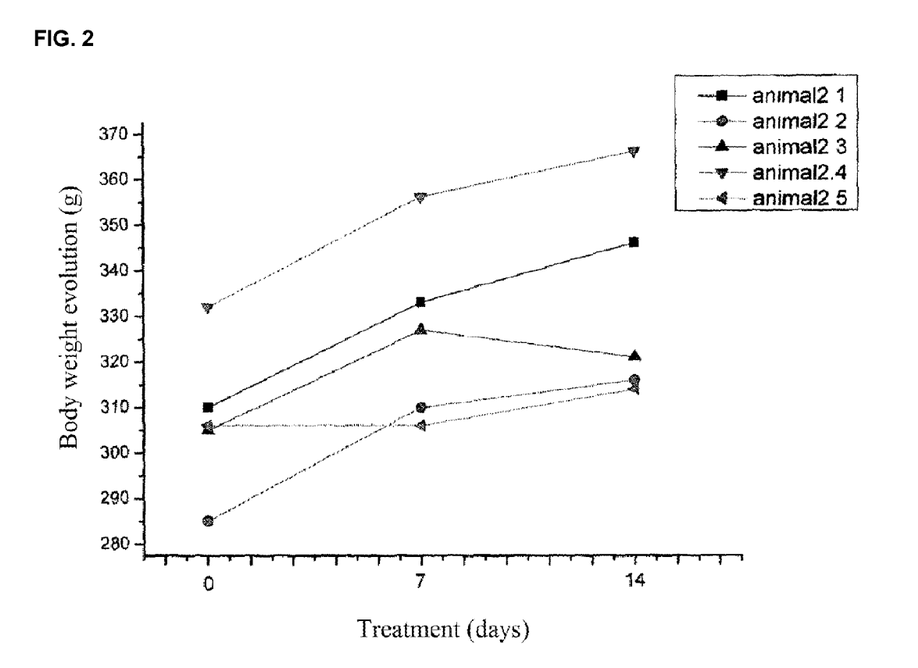
FIG. 2 shows the effect of acute oral administration in Wistar/Uni mice on the evolution of body weight during the 14 days after a single administration of microparticles of *C. citratus* and *C. martinii* 3:1 (present invention). This result is part of an in vivo toxicity assay.

FIG. 2 shows the animal body weight gain, taking into account the difference of the individual weights at the beginning and the end of the acute toxicity test. When compared with the body weight gain data of Wistar/Uni mice, males, kept in the same environmental conditions and fed with the which formed an experimental unit. The analyzed variables were: animal performance, diarrhea score, and percentage of piglets delivered. The study periods were: I—from 28 to 35; II—from 28 to 49; and III from 28 to 63 days old. The treatments were: 1)—Negative Control—basal diet, 2)—Antibiotic—basal diet plus growth promoter MSD 08 63 g/ton of feed (5 ppm), 3)—Test—basal diet plus CB006-S 2.000 g/ton of feed.

The performance results of the piglets during the first period (8 to 35 days) are shown in Table 4 for different groups.

TABLE 4

Initial weight, final weight, average daily gain (GMDP), average daily feed intake (CMDR) and feed conversion (CA) averages of piglets for the period 1 - from 28 to 35 days old.

| Group | Initial weight | Final weight | GMDP 28 to 35 | CMDR 28 to 35 | CA 28 to 35 |
|---|---|---|---|---|---|
| 1 | 7.55a | 9.01a | 0.183a | 0.299a | 1.81a |
| 2 | 7.56a | 9.39a | 0.228a | 0.318a | 1.44a |
| 3 | 7.48a | 8.86a | 0.172a | 0.303a | 2.23a |
| CV % | 2.64 | 6.21 | 36.31 | 10.91 | 49.93 |

Averages followed by the same letter in the columns do not differ by Tukey test (P>0.05).

The performance results of the piglets during period 1 showed no significant difference between groups.

The performance results of the piglets during period 2 (28 to 49 days) are shown in Table 5, for different groups.

TABLE 5

Initial weight, final weight, average daily gain (GMDP), average daily feed intake (CMDR) and feed conversion (CA) averages of piglets for period 2 of the 28 to 49 days old.

| Group | Initial weight | Final weight | GMDP 28 to 49 | CMDR 28 to 49 | CA 28 to 49 |
|---|---|---|---|---|---|
| 1 | 7.56 | 13.31b | 0.274b | 0.371b | 1.94a |
| 2 | 7.54 | 15.12a | 0.360a | 0.539a | 1.51a |
| 3 | 7.48 | 14.16ab | 0.318ab | 0.537a | 1.74a |
| CV % | 2.64 | 9.47 | 19.64 | 14.81 | 6.28 |

Averages followed by the same letter in the columns do not differ by Tukey test (P>0.05).

Performance results for the GMDP and final weight showed significant difference (P>0.05) in favor of group 2, even though group 3 was not statistically different from groups 1 and 2; however, the CMDR was significantly lower for group 1 when compared to the other groups, and between groups 2 and 3 there was no significant difference. There was no significant difference about feed conversion between the tested groups.

The performance results of the piglets during period 3 (from 28 to 63 days) are shown in Table 6 for the different groups.

TABLE 6

Initial weight, final weight, average daily gain (GMDP), average daily feed intake (CMDR) and feed conversion (CA) averages of piglets for the total period 28-63 days of age.

| Group | Initial weight | Final weight | GMDP 28 to 63 | CMDR 28 to 63 | CA 28 to 63 |
|---|---|---|---|---|---|
| 1 | 7.55 | 20.41b | 0.369b | 0.672b | 1.84a |
| 2 | 7.56 | 21.34ab | 0.393ab | 0.714a | 1.82a |
| 3 | 7.48 | 22.81a | 0.437a | 0.722a | 1.65a |
| CV % | 2.64 | 6.59 | 9.80 | 4.44 | 9.49 |

Averages followed by the same letter in the columns do not differ by Tukey test (P>0.05).

The results showed that the final weight was higher in Group 3, while group 2 did not differ statistically from groups 1 and 3; the same results were observed for GMDP. For CMDR, groups 2 and 3 did not differ statistically between themselves, but were higher than group 1. For feed conversion parameter there was no difference between groups in this period.

There was no statistical difference between the groups in relation with the diarrhea incidence and the percentage of piglets delivered to units of growth and termination (Table 7) was not influenced (P<0.05) by experimental treatments, noting that in all groups the percentage of delivered animals was within the desired standards (80-85%) for a pig farming system adopted by agribusinesses.

TABLE 7

Total animals per group, number of dead animals, number of wasted animals and % of delivered animals to the growing and termination, as per different experimental groups.

| Groups | Total number of animals at 63 days | Total number of dead animals | Number of not delivered/ wasted animals | % of delivered animals |
|---|---|---|---|---|
| 1 | 23 | 1 | 3 | 86.95 |
| 2 | 24 | — | 3 | 87.5 |
| 3 | 23 | 1 | 2 | 91.30 |

In the experimental conditions, the additive CB006-S showed similar results to antibiotic MSD08 and superior to control in piglets' performance, in the period of 28-63 days of age showing that it can be used in diets for weanling piglets as possible substitute to antibiotics used in this phase. No animal showed signs of intoxication after ingestion of the tested product.

REFERENCES

Hur, J.; Lee, J. H. Comparative evaluation of a vaccine candidate expressing enterotoxigenico *Escherichia coli* (ETEC) adhesins for collibacilosis with a commercial vaccine using a pig model. *Vaccine*, v. 30, p. 3829-3833, 2012.

Wu, S.; Zhang, F.; Huang, z.; Liu, H.; Xie, C.; Zhang, J.; Thacker, P. A.; Qiao, S. Effects of the antimicrobial peptide cecropin AD on performance and intestinal health in weaned piglets challenged with *Escherichia coli. Peptides*, v. 35, p. 225-230, 2012.

Hayat, A. M.; Tribble, D. R.; Sanders, J. W.; Faix, D. J.; Shiau, D.; Armstrong, A. W.; Riddle, M. S. Knowledge, attitudes, and practice of travelers' diarrhea management among frontline providers. *Journal of Travel Medicine*, v. 18 (5), p. 310-317, 2011.

Licht, T. R.; Ebersbach, T, Frokiaer, H. Prebiotics for prevention of gut infection. *Trends in Food Science & Technology*, v. 23, p. 70-82, 2012.

Li, S. Y.; Ru, Y. J.; Liu, M.; Xu, B.; Péron, A.; Shi, X. G. The effect of essential oils on performance, immunity and gut microbial population in weaner pigs. Livestock Science, v. 145, p. 119-123, 2012.

Junior, V. F. V.; Pinto, A. C.; Maciel, M. A. M. Plantas medicinas, cura segura? Quimica Nova, v. 28 (3), 519-528, 2005.

Skehan P., Storeng R., Scudiero D., Monks A., McMahon J., Vistica D., Warren J. T., Bokesch H., Kenney S., Boyd M. R. New colorimetric citotoxicity assay for anticancer-drug screening. Journal of the National Cancer Institute, v. 82 (13), p. 1107-1118, 1990.

Fouche, G.; Cragg, G. M.; Pillay, P.; Kolesnikova, N.; Maharaj, V. J.; Senabe, J. In vitro anticancer screening of South African plants. Journal of Ethnopharmacology, v. 119, p. 455-461, 2008.

Shoemaker, R. H. The NCI60 human tumour cell line anticancer drug screen. Nat Ver Cancer, V. 6, p. 813-823, 2006.

OECD GUIDELINE FOR TESTING OF CHEMICALS—Acute Oral Toxicity: 420—adopted Dec. 17, 2001. "Sistema Globalmente Harmonizado de Classificação e Rotulagem de Substâncias Quimicas" (Globally Harmonized System of Classification and Labelling of Chemicals—GHS)—http://www.unece.org/trans/danger/publi/ghs/officialtext.html.

Rodrigues, R A F Preparo, caracterização e avaliação funcional de microcápsulas obtidas por spray drying, contendo extrato de café crioconcentrado. Fac Eng Alimentos UNICAMP, 2004.

The invention claimed is:

1. A microparticle comprising *Cymbopogon citratus* essential oil, *Cymbopogon martinii* essential oil, microparticle wall material, and emulsifying agent; wherein the microparticle has a size between 100 and 1000 microns and the weight-to-weight ratio of *Cymbopogon citratus* essential oil to *Cymbopogon martinii* essential oil is selected from the group consisting of 1:3, 1:1, and 3:1.

2. The microparticle according to claim 1, wherein the ratio of *Cymbopogon citratus* essential oil to *Cymbopogon martini* essential oil is 3:1.

3. The microparticle according to claim 1, wherein the wall material comprises at least one of arabic gum, maltodextrin, chitosan, cashew tree gum, and mixtures thereof.

4. The microparticle according to claim 3, wherein the wall material comprises maltodextrin.

5. The microparticle according to claim 1, wherein the emulsifying agent is selected from the group consisting of Tween 80, Tween 60, Tween 20, and soy lecithin.

6. The microparticle according to claim 5, wherein the emulsifying agent comprises Tween 80.

7. The microparticle according to claim 1, wherein the microparticle has a substantially spherical shape.

8. A method of treating gastrointestinal tract infection in a human or an animal comprising administration of a microparticle comprising *Cymbopogon citratus* essential oil, *Cymbopogon martinii* essential oil, microparticle wall material, and emulsifying agent; wherein the microparticle has a size between 100 and 1000 microns and the weight-to-weight ratio of *Cymbopogon citratus* essential oil to *Cymbopogon martini* essential oil is selected from the group consisting of 1:3, 1:1, and 3:1.

9. The method, according to claim 8, wherein the microparticle when administered to a human or animal in need thereof, is administered without an additional vehicle or excipient.

10. The method, according to claim 8, wherein the microparticle when administered to a human or animal in need thereof, is delivered in one of a tablet, an emulsion, a suspension, and a gel capsule.

11. The method, according to claim 8, wherein the microparticle when administered to a human or animal in need thereof, is delivered by mixing with one of water, food, and animal feed.

* * * * *